United States Patent
Eritzland et al.

(10) Patent No.: US 9,339,667 B2
(45) Date of Patent: May 17, 2016

(54) MIXTURE OF INORGANIC COMPOUNDS, PREPARATIONS CONTAINING THE MIXTURE AND USE OF THE MIXTURE

(75) Inventors: Rune Eritzland, Stavanger (NO); Harald Molnes, Stavanger (NO)

(73) Assignee: Sea QIQ AS (NO)

( * ) Notice: Subject to any disclaimer, the term of this patent is extended or adjusted under 35 U.S.C. 154(b) by 504 days.

(21) Appl. No.: 13/138,448

(22) PCT Filed: Feb. 17, 2010

(86) PCT No.: PCT/NO2010/000060
§ 371 (c)(1),
(2), (4) Date: Aug. 17, 2011

(87) PCT Pub. No.: WO2010/095950
PCT Pub. Date: Aug. 26, 2010

(65) Prior Publication Data
US 2011/0300238 A1    Dec. 8, 2011

(30) Foreign Application Priority Data

Feb. 18, 2009    (NO) .................................... 20090781

(51) Int. Cl.
| | | |
|---|---|---|
| *A61Q 19/00* | (2006.01) | |
| *A61K 8/19* | (2006.01) | |
| *A61K 33/08* | (2006.01) | |
| *A61K 33/14* | (2006.01) | |

(52) U.S. Cl.
CPC . *A61Q 19/00* (2013.01); *A61K 8/19* (2013.01); *A61K 33/08* (2013.01); *A61K 33/14* (2013.01); *A61K 2800/592* (2013.01); *A61K 2800/75* (2013.01)

(58) Field of Classification Search
None
See application file for complete search history.

(56) References Cited

U.S. PATENT DOCUMENTS

| | | |
|---|---|---|
| 3,567,378 A | 3/1971 | Ferris |
| 2004/0076687 A1* | 4/2004 | Thompson .................... 424/680 |

FOREIGN PATENT DOCUMENTS

| | | |
|---|---|---|
| DE | 3712505 | 4/1988 |
| EP | 937453 | 8/1999 |
| EP | 1074245 | 2/2001 |
| FR | 2931361 | 7/2008 |
| JP | 8231382 | 9/1996 |
| JP | 2002338242 | 11/2002 |

OTHER PUBLICATIONS

E. Proksh et al., "Bathing in a magnesium-rich Dead Sea salt . . . ", International Journal of Dermatology, 2005, 44, p. 151-157. Abstract, p. 156.

* cited by examiner

*Primary Examiner* — Robert A Wax
*Assistant Examiner* — Thor Nielsen
(74) *Attorney, Agent, or Firm* — Patents + TMS, P.C.

(57) ABSTRACT

A mineral mixture including at least' MgO and its equilibrium of $Mg(OH)_2$, and $MgCl_2$, in which $MgO$—$Mg(OH)_2$ constitutes between 85 and 99.99% by weight; and $MgCl_2$ constitutes between 0.01 and 15% by weight of the magnesium compounds in the mineral mixture. Preparations containing the salt mixture and the use of the mineral mixture for the production of a pharmaceutical preparation for the prevention or therapy of a condition, the condition being undesired eczema or psoriasis, are also described.

11 Claims, No Drawings

MIXTURE OF INORGANIC COMPOUNDS, PREPARATIONS CONTAINING THE MIXTURE AND USE OF THE MIXTURE

The invention relates to a mixture of inorganic oxides, hydroxides and salts and utilization of the mixture for use in cosmetics and skin-care products. More particularly, the invention relates to a mixture of magnesium oxide-magnesium hydroxide, magnesium salts and possibly other minerals for use in preparations which may be used on skin exhibiting eczema, such as atopic eczema, seborrhoeic eczema, hand eczema or contact eczema, and skin exhibiting psoriasis.

In what follows, inorganic compounds in the form of salts, hydroxides and oxides will be referred to as minerals. Any mixture consisting of salts, hydroxides or oxides will be referred to as a mineral mixture. Where appropriate, the particular salt, hydroxide or oxide will be specified.

In an aqueous solution of $Mg(OH)_2$, equilibrium between MgO and $Mg(OH)_2$ will establish itself, the equilibrium depending on the pH of the solution and the amount of minerals in the solution. In what follows, the notation MgO—Mg$(OH)_2$ will be used to indicate the total amount of magnesium oxide and magnesium hydroxide in the mineral mixture.

Zinc oxide, ZnO, has inflammation-subduing, drying and cooling effects on skin. Zinc oxide can be used by up to 25% in creams, ointments and lotions. In particular, it is known to use zinc oxide in connection with the treatment of diaper sores.

It is known that natural mineral mixtures produced by water evaporation from regular sea water has been used in so-called bathroom products, such as bath salts, salt scrubs and soaps.

The addition of such mineral mixtures to cosmetics, including make-up as well, is also known.

Naturally occurring inorganic minerals for use in cosmetics and pharmaceutical products are characterized by giving mild effects as each single inorganic mineral is present at low concentration. This reduces the risk of an acute toxic effect.

Mineral mixtures produced by concentration from sea water are characterized by high contents of halides, mainly chlorides is but also, to some extent, bromides. The electrical conductivity of such mineral mixtures correlates positively with the halide content. Up to 97% of the halides in sea water are constituted by sodium chloride, NaCl. A high proportion of halides in a mineral mixture is unsuitable in many cosmetic and pharmaceutical products. A high content of halides leads to skin irritation, stinging pain from sores and drying-out of the skin.

Further, it is known to use preparations of so-called Dead Sea salt for application on skin exhibiting eczema or psoriasis. It is further known that bathing in the Dead Sea may have a favourable effect on skin which exhibits eczema or psoriasis. According to Ma'or et al. (2006. Int. J. Dermatol. 45: 504-511) the water of the Dead Sea contains, per litre: 230.4 g chlorine and bromine; 45.9 g magnesium; 36.6 g sodium and 7.8 g potassium. In the preparations sold as Dead Sea salt, water from the Dead Sea is not included, but Dead Sea mud rich in minerals. According to the same source, this mud contains the following composition: silicon oxide 20%, calcium oxide 15.5%; aluminium oxide 4.8%; magnesium oxide 4.5%; iron (III) oxide 2.8%; sodium oxide 1.7%; potassium oxide 1.3%; titanium (IV) oxide 0.5%; sulphur trioxide 0.4%; phosphorus pentoxide 0.3%; chlorine 6.7% and bromine 0.2%.

The water of the Dead Sea thus contains a relatively low NaCl content, usually 12-18% and a relatively high content of magnesium halides, mainly $MgCl_2$ and $MgBr_2$. It has been reported that bathing in salt solutions with a relatively high content of magnesium strengthens the skin barrier function, increases the moisture content in skin and reduces inflammation to skin that exhibits atopic eczema (Proksch et al. 2005. Int. J. Dermatol. 44: 151-157; Proksch et al., 2005. Int. J. Dermatol. 44: 177-179).

From the patent document JP2002338242 it is known to use sea water as a basis for producing a mineral mixture consisting of oxides. Minerals are concentrated from filtered sea water by reverse osmosis. Then sodium chloride is removed from the concentrate by nanofiltration. The mineral concentrate is spray-dried and then calcinated at 800-1200° C. for the mixture to have a high content of oxides. The mineral mixture contains 55 to 75% by weight of MgO and 15-30% by weight of CaO. The mineral mixture can be used as a mineral supplement in cosmetics, pharmaceutical products and foodstuffs, for bath salts, for so-called thalassotherapy and for agricultural purposes as an animal product, a fertilizer and a soil-improving agent. The mineral mixture described has a high content of CaO, which is highly water reactive, which may be unfortunate when such a mineral mixture is used in skin-care preparations.

There is a need for a mineral mixture which exhibits a high content of magnesium compounds in particular, which has low conductivity and thereby little skin-irritating effect, for the production of skin-care products and cosmetics.

The invention has for its object to remedy or reduce at least one of the drawbacks of the prior art, or at least provide a useful alternative to the prior art.

The object is achieved through features which are specified in the description below and in the claims that follow.

The present invention contains magnesium in the form of magnesium oxide MgO and magnesium hydroxide, Mg$(OH)_2$. MgO—Mg$(OH)_2$ constitutes the main component of the mixture. Magnesium oxide and magnesium hydroxide give less smarting pain in skin as compared to the use of magnesium chloride or magnesium bromide. Magnesium oxide is also characterized by having low electrical conductivity, a property which is utilized when MgO is used as an insulator in fuses. Magnesium oxide and magnesium hydroxide also have low electrical conductivity in moist or wet condition. Even with the admixture of halides like chlorine and bromine, magnesium oxide will be electrically insulating as long as MgO—Mg$(OH)_2$ constitutes at least 60% of the mixture.

In a first aspect, the invention relates to a mineral mixture including at least MgO and its equilibrium of Mg$(OH)_2$. This equilibrium will establish itself in relation to physiochemical conditions of the mixture, for example the pH value of an aqueous solution and the concentration of MgO—Mg$(OH)_2$ and other minerals. The mineral mixture further includes at least $MgCl_2$. The mineral mixture is characterized by the amount of MgO—Mg$(OH)_2$ constituting between 85 and 99.99% by weight of the magnesium compounds in the mineral mixture and by $MgCl_2$ constituting between 0.01 and 15% by weight of the magnesium compounds in the mineral mixture.

The mineral mixture may also include NaCl. The mineral mixture may also include a group of other minerals. In the mineral mixture, the content of MgO—Mg$(OH)_2$ may constitute between 63 and 80% by weight of the mixture; preferably, MgO—Mg$(OH)_2$ may constitute between 72 and 77% by weight of the mixture; still more preferably, MgO—Mg$(OH)_2$ may constitute between 70-75% by weight of the mixture; NaCl may constitute between 15 and 31% by weight of the mixture; preferably, NaCl may constitute between 18 to 23% by weight of the mixture; $MgCl_2$ may constitute between 0.01 and 11% by weight of the mixture; preferably, $MgCl_2$ may constitute between 0.01 to 4% by weight of the mixture; and a group comprising other minerals may constitute between 0 and 7% by weight of the mixture; preferably, the group of other minerals may constitute between 0 and 2% by weight of the mixture. The group of other minerals may be formed mainly by, for example, $SiO_2$, $CaSO_4$, NaBr, and $MgBr_2$, and preferably, each of the minerals in the group of other minerals may constitute between 0 and 1% by weight of the mineral mixture.

In an alternative embodiment, the mineral mixture may be constituted by MgO—$Mg(OH)_2$ and halide salts and other salts, and in such a way that the ratio by weight between MgO—$Mg(OH)_2$ and the halide salts may be greater than 2.7. In a further alternative embodiment, the ratio by weight between MgO—$Mg(OH)_2$ and the halide salts may be between 2.7 and 2.9.

In a second aspect, the invention relates to the use of a mineral mixture as described, for the production of preparations like cosmetics and skin-care preparations. The skin-care preparations may belong to the group consisting of cream, ointment, lotion and paste. The skin-care preparations may be intended for external use and for dental hygiene use. The mineral mixture may be used as such for the production of cosmetics, including make-up, and skin-care preparations. In an alternative embodiment, the mixture may be ground and the particles size-fractioned, so that the desired particle size can be used for the production of cosmetics and skin-care preparations. In an alternative embodiment, the cream, ointment, lotion or paste produced, containing the mineral mixture, can be used as part of ready-to-use cosmetics or skin-care preparations.

The invention may also relate to a preparation for the prevention or therapy of a skin disease in mammals, including human beings, characterized by undesired eczema or psoriasis. The preparation may contain a pharmaceutically acceptable carrier and a pharmaceutically effective amount of a mineral mixture as described above.

In a third aspect, the invention relates to the use of a mineral mixture as described above for the production of a pharmaceutical preparation for the prevention or therapy of a skin disease, the skin disease being undesired eczema or psoriasis. The eczema may be selected from a group consisting of: atopic eczema, seborrhoeic eczema, hand eczema and contact eczema.

In what follows are described examples of preferred embodiments.

EXAMPLE 1

Natural sea water in a suitable container is subjected to a voltage of 6 volts. A mixture of mainly $Mg(OH)_2$, NaCl and $MgCl_2$ is precipitated onto the cathode. This mixture is transferred to a settling tank, stored and centrifuged. The substance will then have a solids content of 40-60% by weight and a pH value of between 10.0-10.5. The wet substance is dried further and homogenized.

The composition of the substance was determined by means of Inductively Coupled Plasma (IPC). Based on the results from repeated experiments with the production of the substance from sea water and subsequent IPC analysis, general stoichiometry and the use of weight balances, it has been calculated that on a solids basis, the substance is composed of MgO—$Mg(OH)_2$, NaCl, $MgCl_2$ and other minerals. More particularly, the MgO—$Mg(OH)_2$ content is between 63 and 80% by weight, NaCl between 15 and 31% by weight, $MgCl_2$ between 0.01 and 11% by weight while other minerals and possibly other solid components constitute between 0 and 7% by is weight. Other minerals may be constituted by $SiO_2$, $CaSO_4$, NaBr and $MgBr_2$.

By optimization of the process, the composition could be kept within a composition of MgO—$Mg(OH)_2$ between 70 and 77% by weight, NaCl between 18 and 23% by weight, $MgCl_2$ between 0.01 and 4% by weight while other minerals and possibly other solid components constitute between 0 and 2% by weight.

By further optimization of the process, the composition could be kept within a composition of MgO—$Mg(OH)_2$ between 70 and 75% by weight, NaCl between 18 and 23% by weight, $MgCl_2$ between 0.01 and 4% by weight while other minerals and possibly other solid components constitute between 0 and 2% by weight.

Making one portion, the composition was MgO—$Mg(OH)_2$ 72% by weight; NaCl 23% by weight; $MgCl_2$ 4% by weight and other minerals 1% by weight. Stored at room temperature, a water phase above the mineral mixture got a pH value of 10.2. The electrical resistance of the wet mineral mixture was 8.5 k$\Omega$/cm.

EXAMPLE 2

Commercial products of MgO, NaCl and $MgCl_2$ are mixed in the proportions by weight of: MgO 73% by weight; NaCl 23% by weight; and $MgCl_2$ 4% by weight. Stored at room temperature, a water phase above the mineral mixture got a pH value of 11.1.

EXAMPLE 3

Sea salt, which has been produced by the evaporation of sea water, is mixed with the commercial products MgO and $MgCl_2$. The mineral mixture has the following composition: MgO—$Mg(OH)_2$ 72% by weight; NaCl 23% by weight; $MgCl_2$ 4% by weight; other minerals 1% by weight.

EXAMPLE 4

As it is known that halide salts lead to skin irritation, stinging pain from sores and drying-out of the skin, it may be advantageous to state the ratio between MgO—$Mg(OH)_2$ and halides in the mineral mixture when the mineral mixture is produced, at least partially, from sea water as shown in examples 1 and 3. A mineral mixture may be produced in such a way that the weight ratio between MgO—$Mg(OH)_2$ and halides is greater than 2.7. An example of such a mineral mixture in which the ratio is between 2.7 and 2.9 is given by: MgO—$Mg(OH)_2$ between 70 and 75% by weight, NaCl between 18 and 23% by weight; $MgCl_2$ between 0.01 and 4% by weight while other minerals and possibly other solid components constitute between 0 and 2% by weight.

EXAMPLE 5

NaCl as such does not have any specific effect when applied to skin that exhibits eczema or psoriasis. An alternative mineral mixture to the one produced in example 2 would be such a mixture of MgO and $MgCl_2$ that MgO constitutes 95% by weight and $MgCl_2$ constitutes 5% by weight of the mixture.

EXAMPLE 6

For clinical testing, a skin-care cream was produced containing 36% by weight of the mineral mixture: MgO—Mg (OH)$_2$ 72% by weight; NaCl 23% by weight; MgCl$_2$ 4% by weight and other minerals 1% by weight as described in example 1. The skin-care cream consisted of ingredients which are known in the art: water, glycerine, MCT (medium chain triglycerides) oil, purified peanut oil, *Butyrospermum parkii*, hydrolyzed starch, cetaryl alcohol, cetyl alcohol, cetyl stearyl alcohol, carbamide, vegetable saponine, *Centella asiatica*, tecoferyl acetate, retinyl palmitate and fenoxy ethanol.

EXAMPLE 7

In the example is used a cream produced in accordance with example 6.

The test subject was a woman between 40 and 45 years old. She has got psoriasis and atopic eczema. During a psoriasis eruption she has a rash with scaly skin, fever, swollen glands and swollen joints, inter alia swelling of the hands. She has also got suppuration from the portions having rashes. The rash is accompanied by painful itching and a pressing and prickling sensation.

Earlier, during eruptions, she has treated the skin with potassium permanganate and ointments containing cortisone as an active ingredient. She has tried to limit the use of ointments containing cortisone as much as possible as they give thin skin, which is a known side effect.

During a psoriasis eruption on the hands, characterized by scaly skin and accompanied by running sores and severe swollenness, the cream was applied to the hands. Within 24 hours, the swollenness had greatly gone down and the painful itching was gone. After 4 days of treatment with the cream, the skin had healed up with no suppuration, the scaly skin had gone back to normal-looking skin and the swelling was all gone.

The invention claimed is:

1. A mineral mixture comprising:
    MgO;
    an amount of Mg(OH)$_2$ to establish an equilibrium with the MgO when the mineral mixture is hydrated prior to drying the mineral mixture;
    MgCl$_2$ wherein a total amount of the MgO and the Mg(OH)$_2$ constitutes between 63 and 80% by weight of the mineral mixture and further wherein the MgCl$_2$ constitutes between 0.01% and 11% by weight of the mineral mixture;
    NaCl that constitutes between 15% and 31% by weight of the mineral mixture wherein MgO, Mg(OH)$_2$, MgCl$_2$ and NaCl collectively constitute between 93% and 100% of the mineral mixture; and
    other minerals constituting between 0% and 7% by weight of the mineral mixture wherein the other minerals include SiO$_2$, CaSO$_4$, NaBr and MgBr$_2$ wherein the mineral mixture has a ratio greater than 5.4:1 of Mg:Ca by weight.

2. The mineral mixture of claim 1 wherein the total amount of the MgO and the Mg(OH)$_2$ constitutes between 70 and 77% by weight of the mineral mixture wherein the NaCl constitutes between 18% and 23% by weight of the mineral mixture wherein the MgCl$_2$ constitutes between 0.01% and 4% by weight of the mineral mixture and further wherein the other minerals constitute between 0% and 2% by weight of the mineral mixture.

3. The mineral mixture of claim 1 wherein the total amount of the MgO and the Mg(OH)$_2$ constitutes between 63% and 75% by weight of the mineral mixture wherein the NaCl constitutes between 18% and 23% by weight of the mineral mixture wherein the MgCl$_2$ constitutes between 0.01% and 4% by weight of the mineral mixture and further wherein the other minerals constitute between 0% and 2% by weight of the mineral mixture.

4. The mineral mixture of claim 1 wherein SiO$_2$, CaSO$_4$, NaBr and MgBr$_2$ each constitutes between 0% and 1% by weight of the mineral mixture.

5. A preparation having a mineral mixture with magnesium compounds, wherein the preparation comprises:
    MgO;
    an amount of Mg(OH)$_2$ to establish an equilibrium with the MgO when the mineral mixture is hydrated prior to drying the mineral mixture;
    MgCl$_2$ wherein a total amount of the MgO and the Mg(OH)$_2$ constitutes between 63% and 80% by weight of the mineral mixture and further wherein the MgCl$_2$ constitutes between 0.01% and 11% by weight of the mineral mixture;
    NaCl that constitutes between 15% and 31% by weight of the mineral mixture wherein MgO, Mg(OH)$_2$, MgCl$_2$ and NaCl collectively constitute between 93% and 100% of the mineral mixture; and
    other minerals constituting between 0% and 7% by weight of the mineral mixture wherein the other minerals include SiO$_2$, CaSO$_4$, NaBr and MgBr$_2$ wherein the mineral mixture has a ratio greater than 5.4:1 of Mg:Ca by weight.

6. The preparation of claim 5 wherein the preparation belongs to the group consisting of cosmetics, creams, ointments, lotions and pastes.

7. The preparation of claim 5, further comprising:
    a pharmaceutically acceptable carrier; and
    a pharmaceutically effective amount of the mineral mixture for the prevention and therapy of a skin disease in a mammal wherein the skin disease is selected from the group consisting of an undesired eczema and an undesired psoriasis.

8. A method for producing a preparation with a mineral mixture wherein the preparation is for the prevention and therapy of a skin disease being at least one member of the group consisting of undesired eczema and undesired psoriasis, the method comprising the steps of:
    forming the mineral mixture with MgO, an amount of Mg(OH)$_2$ to establish an equilibrium with the MgO when the mineral mixture is hydrated prior to drying the mineral mixture, MgCl$_2$, NaCl and other minerals wherein a total amount of the MgO and the Mg(OH)$_2$ constitutes between 63% and 80% by weight of the mineral mixture wherein the MgCl$_2$ constitutes between 0.01% and 11% by weight of the mineral mixture wherein the NaCl constitutes between 15% and 31% by weight of the mineral mixture and further wherein the other minerals constitute between 0% and 7% by weight of the mineral mixture wherein the other minerals include SiO$_2$, CaSO$_4$, NaBr and MgBr$_2$ wherein the mineral mixture has a ratio greater than 5.4:1 of Mg:Ca by weight; and
    combining the mineral mixture with a pharmaceutically acceptable carrier for treating the skin disease.

9. The method of claim 8 wherein the undesired eczema is selected from a group consisting of atopic eczema, seborrhoeic eczema, hand eczema and contact eczema.

10. A mineral mixture comprising:
    MgO;
    Mg(OH)$_2$;
    MgCl$_2$ wherein a total amount of the MgO and the Mg(OH)$_2$ constitutes between 63% and 80% by weight of the mineral mixture and further wherein the $MgCl_2$ constitutes between 0.01% and 11% by weight of the mineral mixture;

NaCl that constitutes between 15% and 31% by weight of the mineral mixture wherein MgO, $Mg(OH)_2$, $MgCl_2$ and NaCl collectively constitute between 93% and 100% of the mineral mixture; and a group of other minerals that constitutes between 0% and 7% by weight of the mineral mixture wherein the group of other minerals includes $SiO_2$, $CaSO_4$, NaBr and $MgBr_2$ wherein the mineral mixture has a ratio greater than 5.4:1 of Mg:Ca by weight.

11. A mineral mixture comprising:

MgO;

$Mg(OH)_2$;

$MgCl_2$ wherein a total amount of the MgO and the $Mg(OH)_2$ constitutes between 63% and 80% by weight of the mineral mixture and further wherein the $MgCl_2$ constitutes between 0.01% and 11% by weight of the mineral mixture;

NaCl that constitutes between 15% and 31% by weight of the mineral mixture wherein MgO, $Mg(OH)_2$, $MgCl_2$ and NaCl collectively constitute between 93% and 100% of the mineral mixture; and other minerals constituting between 0% and 7% by weight of the mineral mixture wherein the mineral mixture has a ratio greater than 5.4:1 of Mg:Ca by weight.

* * * * *